United States Patent [19]

Fox et al.

[11] Patent Number: 4,485,244

[45] Date of Patent: Nov. 27, 1984

[54] THERMAL PROCESS FOR THE LIQUEFACTION OF AROMATIC HYDROCARBON OXIDATION RESIDUES AND RECOVERY OF ACETIC ACID

[75] Inventors: Joseph D. Fox; George E. Kuhlmann, both of Naperville; John G. Hundley, St. Charles, all of Ill.

[73] Assignee: The Standard Oil Company, Chicago, Ill.

[21] Appl. No.: 438,742

[22] Filed: Nov. 3, 1982

[51] Int. Cl.$^3$ .............................................. C07D 307/89
[52] U.S. Cl. ...................................... 549/245; 549/250; 549/251; 562/479; 562/485; 562/487; 562/494
[58] Field of Search ........................ 549/245, 250, 251; 562/479, 485, 487, 494

[56] References Cited

U.S. PATENT DOCUMENTS

| | | | |
|---|---|---|---|
| 3,853,924 | 12/1974 | Meyer et al. | 549/245 |
| 3,948,956 | 4/1976 | Handrick | 549/245 |
| 4,215,055 | 7/1980 | Palmer et al. | 549/250 |
| 4,234,494 | 11/1980 | Schroeder et al. | 549/251 |

Primary Examiner—Richard L. Raymond
Attorney, Agent, or Firm—Gunar J. Blumberg; William T. McClain; William H. Magidson

[57] ABSTRACT

A thermal process for the decarboxylation and dehydration of aromatic acid residue to convert such residue to grindable form and recover the solvent of reaction therefrom.

13 Claims, No Drawings

THERMAL PROCESS FOR THE LIQUEFACTION OF AROMATIC HYDROCARBON OXIDATION RESIDUES AND RECOVERY OF ACETIC ACID

FIELD OF INVENTION

This invention relates to a non-catalytic thermal process for the liquefaction of a solid mixture of oxygen-containing derivatives of mono- and polymethyl benzenes containing a cyclic ester group (e.g., as in phthalide) or one or more aldehyde-, methylol-, or carboxy-nuclear substitutents such as the solid residues obtained in the manufacture of an aromatic di- or tricarboxylic acid which also contains cobalt and/or manganese salts of organic acids and many also contain organic and inorganic bromides. The field of invention also relates to produce grindable residues and the recovery of acetic acid from the residues.

BACKGROUND

The thermal decomposition of benzoic acid to benzene and carbon dioxide begins non-catalytically at 370° C. in a glass bulb and is substantially complete at 400° C. (*Chemical Abstracts*, vol. 41, 646) according to the original article of Wolfgang Mosher in *Helv. Chem. Acta.* 14, 971–97 (1931) and such dissociation is accelerated by copper and cadmium catalysts. Said dissociation occurs at temperatures as low as 245° to 250° C. in the presence of Zn-Cu-Cr oxide-type catalysts according to Corliss R. Kinney and David P. Langlois in *J. Am. Chem. Soc.*, vol. 53, 2189–2192 (1931). Decarboxylation of benzaldehyde to high yields of benzene is aided by plasma of glow discharge according to Published Patent Application ("Offenlegungsschrift") No. 2,038,272 of the Federal German Republic, published Mar. 16, 1972. According to British Pat. No. 735,300, published Aug. 17, 1955, toluic acids heated to 400° C. in the presence of chromites of Zn, Cd, Zn-Cd, Zn-Fe or ZnO with either CuO or CdO are converted to toluene.

From the state of the art at the time of making the present invention it appears that the main interest in decarboxylation of benzene carboxylic acids was to prepare a higher quality benzene carboxylic acid of lesser COOH group content from a benzene carboxylic acid of higher COOH group content and lower quality such as a coal acid or to obtain a benzene carboxylic acid of exceptionally high quality; e.g., pharmaceutical quality benzoic acid, from phthalic anhydride by converting it to o-phthalic acid and decarboxylating it. But there was no apparent interest in the decarboxylation of benzene carboxylic acids to aromatic hydrocarbons.

In an altogether different environment a new problem has arisen. In the commercial manufacture of benzene di- or tricarboxylic acids (e.g., isophthalic acid (IPA), terephthalic acid (TA) or trimellitic acid (TMLA)) there is obtained, after maximizing recovery of such acid and recovery for reuse the reaction solvent, a residue which is a mixture of oxygen-containing derivatives of benzene and toluene which are mono-, di- and tricarboxylic acids, aldehydocarboxylic acids, and methylol-substituted benzene or toluene or their carboxylic (benzoic or toluic) acids and which also contains components of catalysis. Usually such components of catalysis are Co-Mn-Br or Co-Mn-Ce-Br from liquid phase oxidation of a xylene or pseudocumene (1,2,4-trimethylbenzene) with air in the presence of acetic acid reaction solvent. A similar residue is also obtained from the neat oxidation of liquid o-xylene with air in the presence of Co-Mn-Br catalyst system after dehydrating the o-phthalic acid formed to its anhydride under conditions which vaporize the anhydride, water and materials boiling between the anhydride and water. While such residues amount to from 2 to 25 weight percent of the benzene di- or tricarboxylic acid produced, such residue production annually is substantial in view of the millions of kilograms of the benzene di- or tricarboxylic acids produced annually.

Such residues contain water soluble benzene carboxylic acids and water soluble forms of the components of catalysis. Landfill disposal of such residues is undesirable because rain and ground water leach out those carboxylic acids and soluble forms of the components of catalysis and can contaminate surface run off water and eventually streams as well as below surface aquafiers. Disposal of such residues can be made by incineration as disclosed in U.S. Pat. Nos. 4,258,227 and 4,266,084 and use made of the resultant heat produced, but the catalyst components are converted to forms in the resultant ash which are difficult and/or expensive to convert to reusable forms for the oxidation of the methyl-substituted benzenes. Although in such residues the substituted benzene and toluene compounds whose substituents are the carboxy-, aldehyde- and methylol substituents are individually desirable and useful commercial products, it is not economically feasible to separate and recover the individual compounds from the residues.

Based on the knowledge that most of the oxygen-containing aromatic compounds in the residue can be decarboxylated by thermal means, it would be desirable to devise a decarboxylation process which would convert the oxygen-containing aromatic compounds to aromatic hydrocarbons which are volatile under such process conditions so that the hydrocarbon vapors can be readily removed and condensed for their recovery. It is also known that under the severe thermal conditions required for substantially complete decarboxylation to convert the oxygen-containing substituted aromatics to benzene and toluene there can also occur ring coupling (e.g., to form biphenyl) and ring fusion as well as charring of some of the organic compounds.

To use a decarboxylation catalyst for the thermal conversion of the foregoing residues to easily recoverable and useful aromatic hydrocarbons would be desirable providing the use of catalyst does enhance the production of the aromatic hydrocarbons but does not make useless the resulting char or further contaminate the catalyst components present so as to make the recovery of cobalt, the most expensive component, technically and commercially unattractive.

We have in our laboratories investigated the use of various compositions previously suggested as decarboxylation catalyst and found the resulting thermal conversions to be unattractive.

The consistently better prior suggested catalyst was found to be the combination of zinc oxide and alumina. Such catalyst is used at 500° C. with one to two gram samples of terephthalic acid process residues introduced consecutively at about 5-minute intervals into the heated quartz tube containing said catalyst over a five-day period. The liquid aromatic hydrocarbon yield decreases from 26.4 weight percent down to 14.6 weight percent of residue fed over the five-day period and considerable blackening of the catalyst is observed. Said liquid aromatic hydrocarbon decrease occurs with a residue-to-catalyst weight ratio of no more than about 2:1. Such results indicate a very short life for the ZnO—alumina catalyst and that frequent regeneration thereof would be necessary for such catalyst to be used commercially.

Such short useful catalyst life made the use thereof for pyrolysis of the aforementioned residues commercially unattractive. However, the present inventive non-catalytic decarboxylation of the oxygen-containing derivatives of benzene and toluene and especially the cyclic ester, methylol-, aldehyde-, carboxy-, carboxy- and aldehyde-, keto- and carboxy-, and methylol- and carboxy-substituted benzenes obtained as a residue from the manufacture of benzene di- and tricarboxylic acids does not have such disability and is technically and commercially attractive.

STATEMENT OF THE INVENTION

According to the present invention a solid mixture of oxygen containing derivatives of mono- and polymethyl benzenes containing a cyclic ester group or an aldehyde-, methylol-, carboxy-, keto- and carboxy-, methylol- and carboxy, and carboxy- and aldehyde-substituted benzene and toluene and such mixtures from the manufacture of benzene di- and tricarboxylic acids also containing cobalt salt or cobalt and manganese salts or organic acids and, further, sometimes containing organic or inorganic bromides was heated to a temperature of about 500° to about 600° F. to induce decarboxylation reactions and the formation of anhydrides through dehydration.

This process improved the handling characteristics of the residue as a melt by reducing viscosity and by producing brittle residues after cooling to ambient temperature. Our process alters the physical properties of these residues so they become amenable to grinding to a fluidizable solid. Another advantageous feature of our novel process is that it enables us to recover valuable reaction solvents such as acetic acid. Commercial isophthalic acid plants produce a residue stream which contains about 30 to 40 percent solids in aqueous acetic acid. Processing this stream in a Dopp residue kettle at about 430° to about 460° F. can only reduce the acetic acid concentration to about 5 to about 15 weight percent and still maintain fluidity. In the prior art during residue dumping, the acetic acid vapor causes health hazards and requires the area to be evacuated. In prior art this residue is buried. The residue contains up to 15 weight percent acetic acid about 0.01 to about 1.0 weight percent cobalt, about 0.1 to about 10 weight percent manganese, and about 0.1 to about 10 weight percent bromine. The residue from the oxidation process units is difficult to process and handle because the major constituents are high melting acids such as terephthalic acid, isophthalic acid, trimellitic acid and coupled and condensed aromatic acids. Our novel process comprising the heating of the residue at a temperature of about 500° F. to about 600° F. provides a solution for the residue handling problem encountered in commercial aromatic oxidation facilities. We have found that heating the residue at a temperature of about 500° F. to about 600° F. promotes residue fluidity by converting the aromatic acids to their intra and intermolecular anhydrides through dehydration processes and improves the residue mixing and heat transfer to maximize acetic acid removal. Conversion of a portion of the residue to anhydrides is an important feature of our process since anhydrides usually exhibit lower melting points and higher boiling points than their acid precursors. We have discovered that the thermal treatment of the residue at about 500° F. to about 600° F. for one hour has allowed the vaporization of the solvent, usually acetic acid, from the residue and rendered the residue, when cooled, into a brittle and grindable end product from which the catalyst such as cobalt and manganese can be recovered by pyrolysis. In our process residue fluidity is maintained in the absence of a solvent, such as acetic acid, by the formation of lower melting anhydrides from higher melting acids and the decarboxylation of high molecular weight compounds to lower molecular weight products. The temperature range of about 500° F. to about 600° F. is critical since at lower temperatures the acetic acid cannot be removed from the residue mixture and a grindable product cannot be achieved; at temperatures above about 600° F. the residue gives off bromine which can cause corrosion.

Our process can suitably be conducted as a continuous process or a batch process. In the batch process the residue is heated at a temperature of about 500° F. to about 600° F. The solvent is collected, and the liquefied residue is cooled to ambient or room temperature and ground. This ground residue is pyrolyzed to recover cobalt and manganese.

In the continuous process the residue is quickly heated to and maintained at a temperature of about 500° F. to 600° F. until substantially all of the acetic acid contained in the residue is removed and the residue is sufficiently liquefied to be agitated. Additional residue is then added to the molten residue at a rate to afford a residence time of 0.1–24 hours, preferably 1–4 hours, before being continuously withdrawn from the vessel. The continuous process is suitably started in an initially cold vessel by charging the vessel with a suitable heat transfer medium such as oil, phthalic anhydride, trimellitic anhydride, etc., and heating this material to 500° F. to 600° F. Alternatively, heat can advantageously be generated by charging paraffinic hydrocarbons to the vessel along with the residue and introducing enough air or oxygen to oxidize the hydrocarbons to provide the required heat. Rapidly heating the cold residue directly to 500° F. to 600° F. is sufficient as long as adequate provisions are made for a large heat exchange capacity across the vessel walls or through internal heating coils.

The molten residue is continuously exiting the reaction vessel and is advantageously treated in several ways. Among the suitable procedures are to allow the molten residue to cool and then to bury it in a sanitary landfill or to burn it in an incinerator to recover the contained catalyst metals in the ash. The continuous residue treatment process at 500° F. to 600° F. we have discovered allows an incinerator to be continuously fed molten material and, therefore, allows economic use to be made of its fuel value. The molten residue would be maintained at 500° F. to 600° F. during its passage through a transfer pipe to a surge storage tank, and then to the incinerator. Alternatives include preparing a water slurry of the molten residue to extract some of the contained metals prior to pumping the slurry to an incinerator, or cooling and grinding the residue so it could be fluidized by inert gas or air into the incinerator for combustion. Another treatment of the molten residue would heat the material above 600° F., perhaps to 700° F., during a long residence time, such as 4–12 hours, to recover valuable hydrocarbons such as benzene, by extensive pyrolitic decomposition of the residue. The material remaining from this residue treatment process can still be disposed of by incineration or burial in a sanitary landfill.

The following examples illustrate the preferred embodiment of this invention. It will be understood that the examples are for illustrative purposes only and do not purport to be wholly definitive with respect to the conditions of the scope of the invention.

EXAMPLE 1

Residue Liquification Process

Apparatus—The thermal treatment of IPA residue was carried out in a 500 ml oil-heated glass kettle equipped with an agitator, thermocouple wells below and above liquid level, an inert gas inlet, and gas exhaust outlet. The kettle heat exchange medium was Dow-Corning Molykote 710 R Silicon Oil. The exhaust gases passed through an overheat hot-oil jacketed heat exchanger and then into a cold-water cooled heat exchanger prior to a 250 ml glass graduated liquid condensate collector. The overhead heat exchanger oil was AXON 200 CST Silicon Oil which was maintained at 220°–330° F. to regulate the amount of condensible material passed on through to the cold-water heat exchanger. The volume of uncondensed gases was measured on stream by an American Manufacturing Company Model AL-17-1 wet test meter. The rate of gas evolution over short periods of time was measured in a graduated glass gas collection tube by the water displacement method.

The reflux condenser provided for water removal and refluxing of any benzoic acid present initially, or formed by the decarboxylation and decomposition of aromatic acids and high boilers.

The time needed for the residue to reach 500° F. varied from 270 minutes (a slow heat run) to 30 minutes (a fast heat run). The 30 minute fast heat runs were made to simulate a continuous process in which the acetic acid was flashed off. The amount of time the residue stayed at the prescribed run temperature was between 50 and 400 minutes. After this time period, the residue was removed and sent in for analysis.

Results

The experimental data (see in Table I) was obtained from experiments designed to test all reasonable process variations to achieve residue fluidity. It was quickly found that a reaction temperature of about 500° F. assured residue fluidity while a reaction temperature of 450° F. led to a viscous liquid. As long as a 500° F. minimum reactor temperature was maintained, essentially all of the acetic acid presently discarded in residue could be removed.

The dehydration of aromatic acids to anhydrides to maintain fluidity was also achieved. Benzoic acid anhydride, phthalic anhydride, and trimellitic anhydride are all lower melting and higher boiling than their corresponding acids, keeping the residue fluid even in the absence of acetic acid and their formation seems very reasonable.

| Benzoic Acid | Phthalic Acid | Trimellitic Acid (TMLA) |
| --- | --- | --- |
| mp 250° F. | mp 446° F. (dec) | mp 428° F. (dec) |
| bp 482° F. | bp — | bp — |
| Benzoic Anhydride | Phthalic Anhydride | Trimellitic Anhydride |
| mp 108° F. | mp 268° F. | mp 322° F. |
| bp 680° F. | bp 543° F. | bp 464° F. (14 mm) |

As shown in Table 2, when the condenser temperature was adjusted downward to retain more benzoic acid in the reactor (Runs 6430-25P or 29P or 36P), or the reactor temperature and residue time were minimized (Runs 6430-4P or 7P), the amount of benzoic acid in the final residue exceeded by 3–5 times the benzoic acid in the most severely heat-treated product (Run 6430-10P).

Decarboxylation of high melting High Boilers to lower melting aromatic carboxylic acids was successful. Heating the residue to increasingly severe thermal treatment caused up to a 94% decrease in high molecular weight compounds and up to a 28% decrease in hemimellitic acid/trimellitic acid or HMLA/TMLA (see Table 3). The TA/IPA content of the residue rose by up to 36% as a result of the decarboxylation reactions. It is clear that as the combined reactor temperature and residence time increased, the amount of residue decarboxylation increased.

TABLE 1

| ANALYSIS OF HEAT TREATED IPA RESIDUE | | | | | | | | |
| --- | --- | --- | --- | --- | --- | --- | --- | --- |
| Run 6430 | 4J[1] | 4P | 7P | 10P | 18P | 25P | 29P | 36P |
| Sample Charge, g. | — | 490 | 509 | 490 | 500 | 500 | 500 | 500 |
| Start-up Time to 500° F., min. | — | 270 | 125 | 80 | 60 | 30 | 40 | 40 |
| Max. Reactor Temp., °F. | — | 500 | 550 | 600 | 600 | 560 | 550 | 500 |
| Residence Time at Max. Temp., min. | — | 105 | 55 | 165 | 240 | 60 | 120 | 180 |
| Condenser Oil Temp., °F. | — | 305 | 310 | 310 | 334 | 220 | 220 | 220 |
| PRODUCTS: | | | | | | | | |
| Weight of Recovered Residue, g. | — | 423 | 433 | 342 | 352 | 405 | 431 | 445 |
| Weight of Condensables, g. | — | >22 | 15 | 28 | 60 | 38 | 47 | 42 |
| CONDENSABLES: | | | | | | | | |
| Benzoic Acid, wt. % | — | N/A | N/A | N/A | 2.97 | 3.08 | 2.87 | 2.09 |
| Benzene, ppm. | — | 20 | — | — | 620 | — | — | — |
| RECOVERED RESIDUE: | | | | | | | | |
| Co, wt. % | 0.177 | 0.203 | 0.204 | 0.26 | 0.272 | 0.22 | 0.203 | 0.166 |
| Mn, wt. % | 1.57 | 1.85 | 1.78 | 2.25 | 2.28 | 1.90 | 1.74 | 1.48 |
| Br, wt. % | 1.92 | 1.89 | 1.52 | 0.65 | 0.26 | 1.84 | 1.81 | 1.65 |

TABLE 1-continued

| | ANALYSIS OF HEAT TREATED IPA RESIDUE | | | | | | | |
|---|---|---|---|---|---|---|---|---|
| Run 6430 | 4J[1] | 4P | 7P | 10P | 18P | 25P | 29P | 36P |
| Benzoic Acid, wt. % | 10.71 | 6.75 | 8.56 | 2.09 | 2.97 | 5.96 | 10.15 | 10.01 |
| Phthalic Acid (OA), wt. % | 2.66 | 2.02 | 2.15 | 1.28 | 1.11 | 1.96 | 2.47 | 2.56 |
| IPA/TA, wt. % | 30.58 | 35.93 | 33.03 | 41.54 | 40.43 | 39.47 | 38.58 | 34.31 |
| TMLA/HMLA, wt. % | 10.48 | 9.21 | 8.15 | 7.54 | 8.10 | 9.92 | 8.56 | 8.81 |
| High Boilers, wt. % | 15.36 | 12.25 | 6.85 | 0.997 | 0.95 | 12.98 | 10.86 | 16.9 |
| Trace Acetic Acid, wt. % | 3.51 | 0.033 | 0.026 | 0.029 | 0.019 | 0.035 | 0.091 | 0.10 |
| Viscosity at 500° F., CP | — | — | 650 | — | — | 270 | — | — |

[1]IPA Plant Residue which was the starting material for all subsequent runs.

TABLE 2

| RETENTION OF BENZOIC ACID IN THE REACTOR | | | | | | |
|---|---|---|---|---|---|---|
| Run 6430 | 25P | 29P | 36P | 4P | 7P | 10P |
| Run Type | Cooler Reflux Condenser | | | Low Reactor Temp. Short Residence Time | | High Temp. Long Res. Time |
| Max. Reactor Temp., °F. | 560 | 550 | 500 | 500 | 550 | 600 |
| Residence Time, min. | 60 | 120 | 180 | 105 | 55 | 165 |
| Condenser Temp., °F. | 220 | 235 | 225 | 305 | 310 | 310 |
| Benzoic Acid in Residue, wt. % | 5.96 | 10.15 | 10.01 | 6.75 | 8.56 | 2.09 |

TABLE 3

| REDUCTION OF HIGH MOLECULAR WEIGHT COMPOUNDS IN RESIDUE THROUGH THERMAL DECARBOXYLATION | | | | |
|---|---|---|---|---|
| Run 6430- | 4J | 4P | 7P | 10P |
| Run Type | Starting Material | More Severe Thermal Conditions | | |
| Reactor Max. Temp., °F. | — | 500 | 550 | 600 |
| Residence Time | 0 | 105 | 55 | 165 |
| Loss in Residue wt. % | 0 | 14 | 15 | 30 |
| Residue Composition, wt. % | | | | |
| TA/IPA | 30.58 | 35.93 | 33.03 | 41.54 |
| HMLA/TMLA | 10.48 | 9.21 | 8.15 | 7.54 |
| High Molecular Weight Compounds | 15.36 | 12.25 | 6.85 | 0.997 |

EXAMPLE 2

The three feedstocks used in this study were:

(1) IPA Plant residue (Sample No. 6430-4J) that was too moist and tacky to grind.

(2) Feed to the Plant Dopp kettle (Sample WJ-2407, HD-502).

(3) Plant stripper stillpot bottoms (Sample No. GM-80-12, ED-403).

The heat treatment of the IPA residue was carried out in the apparatus described in Example 1. Approximately 500 grams of IPA residue were loaded into the 500 ml resin kettle. The oil bath contained Dow-Corning Molykote 710 R silicon oil which was preheated to 500°-600° F. before the residue was placed in the bath. Vapors coming off were refluxed with a hot oil condenser which was fed by a bath of Axon 200 CST silicon oil kept in a range of 220°-330° F. Vapors not refluxed are condensed in a cold water condenser and the condensate is measured in a graduated gas collection tube. Gas generated ($CO_2$ was identified by a $Ba(OH)_2$ test and was the major component of the gas) was then measured in an American Manufacturing Company Model AL-17-1 wet test meter which was calibrated with air.

The time needed for the residue to reach 500° F. varied from 270 minutes (a slow heat run) to 30 minutes (a fast heat run). The 30 minute fast heat runs were made to simulate a continuous process in which the acetic acid was flashed off. The amount of time the residue stayed at the prescribed run temperature was between 50 and 400 minutes. After this time period, the residue was removed, cooled, and sent in for analysis. There were three analytical tests run on the solid products to determine which reactions were taking place and what affected them, esterification Gas Chromatography (EGC) for Low and High Boilers, X-Ray Fluorescence for Co, Mn, and Br and gas chromatography for trace acetic acid.

Various tests were performed on the condensate. Karl Fischer water tests were done on a few samples, but as the oil condenser temperatures were raised, benzoic acid was distilled rather than refluxed and precipitated in the condensate so the test could not be performed. The tests were then switched to esterification gas chromatography.

A laboratory grinding test to rank residue susceptibility to grinding was devised (Notebook 6430, Page 45). The test procedure was to determine the number of 6 cm drops of a 285.5 g pestle that were required to break a 1 cc piece of residue into pieces no larger than 0.05 cc. The number of drops was then multiplied by 2, allowing for some judgment as to whether a "half drop" would have sufficed, since that was the fewest number of drops ever achieved. The lower the ranking (number of drops×2), the easier the residue was to grind. All the treated residues were so brittle it was clear they are easily ground.

Development of Residue Fluidity

It was decided that the development of residue fluidity depended on three aspects—volatilization of acetic acid, dehydration of aromatic polycarboxylic acids, and decarboxylation of high molecular weight carboxylic acid to lower molecular weight acids such as benzoic acid. The experimental data recorded in Table 4 was obtained from experiments designed to test all reasonable process variations to achieve residue fluidity. It was quickly found that a reaction temperature of 500° F. assured residue fluidity while a reaction temperature of 450° F. led to a viscous liquid. Therefore, a 500° F. minimum reaction temperature was adopted.

The mildest conditions (Run 6430-4P) removed all but trace levels of acetic acid from the residue. As long as a 500° F. minimum reactor temperature was maintained, essentially all of the acetic acid presently discarded in commercial plant residue can be removed.

The dehydration of aromatic acids to anhydrides to maintain fluidity was also achieved. By way of illustration, benzoic acid anhydride, phthalic anhydride, and trimellitic anhydride would all be lower melting than their corresponding acids.

As shown in Table 5, when the condenser temperature was adjusted downward to retain more benzoic acid in the reactor (Runs 6430-25P or 29P or 36P), or the reactor temperature and residue time were minimized (Runs 6430-4P or 7P), the amount of benzoic acid in the final residue exceeded by 3-5 times the benzoic acid in the most severely heat-treated product (Run 6430-10P). Presumably, the retained benzoic acid formed benzoic anhydride in the residue. The conditions which favor benzoic acid retention in the residue are also favored by practical processing considerations because the retained benzoic acid maintains residue fluidity while volatilized benzoic acid could cause fouling and upsets and accumulate in process streams.

Decarboxylation of high melting high molecular weight compounds to lower melting aromatic carboxylic acids was successful. As shown in Table 6, exposure of the starting material residue to increasingly severe thermal treatment caused up to a 94% decrease in High Boilers and up to a 28% decrease in HMLA/TMLA. The TA/IPA content of the residue rose by up to 36% as a result of the decarboxylation reactions. The decarboxylation of the residue contributed up to a 30 wt.% loss in recovered residue weight. It is clear in Table 6 that as the combined reactor temperature and residence time increased, the amount of residue decarboxylation increased. For Run 6430-47P, the loss of $CO_2$ was measured to be 0.41 moles. The material balance closure was 99% including the 4 wt.% residue loss to $CO_2$. Thus the residue heat treatment can be described simply as an acid dehydration, acetic acid volatilization, and high molecular weight compound decarboxylation process. This becomes even clearer when the residue composition before treatment is compared to that after thermal treatment as in Table 7. The more severely treated residues have almost no High Boilers remaining and have had large reductions in OA and HMLA/TMLA content. The IPA/TA content remained higher than the OA content because these acids were apparently produced by High Boiler decarboxylation faster than they were consumed themselves by decarboxylation.

Benzene was produced by the decarboxylation of aromatic acids perhaps catalyzed by the catalyst metals present in the residue. The amount was only 20-620 ppm in the condensables (See Table I) with higher reaction temperatures causing the higher benzene production. Since a 500° F. reactor temperature seems adequate for residue treatment, only trace levels of benzene (<1 ppm of residue) will be encountered as in Run 6430-4P.

Bromine was lost from the residue as it was heated to higher and higher temperatures as shown below and in Table I:

| Sample 6430 | 4J | 4P | 7P | 10P |
|---|---|---|---|---|
| Reactor Temp., °F. | Starting Material | 500 | 550 | 600 |
| Gross Residue Bromine Content, wt. % | 1.92 | 1.89 | 1.52 | 0.65 |
| Residue Bromine Accountability, % | 100 | 85 | 70 | 24 |

The 500° F. run hardly caused any reduction in bromine content, but higher temperatures apparently do drive off significant amounts of bromine. Although a 500° F. reactor temperature will probably suffice for residue treatment, if higher temperatures such as 600° F. are employed, precaution will have to be taken against possible corrosion and other problems caused by the escaping bromine vapors.

Residue Grindability

The thermal treatments of IPA residue always produced brittle and apparently grindable products (see Table 4). The ease of grinding, as determined by a grinding scale discussed in the above, increased with increasing reactor temperature from 500° F. to 600° F. Residue pumpability was similarly improved as judged visually and by the determination of residue viscosity (see Table 4). The IPA residue viscosity range of 270-650 cP at 500° F. is well below that of trimellitic anhydride residue which is routinely pumped at 200-1000 cP. Therefore, thermally induced changes in residue composition, such as the complete loss of acetic acid, were beneficial in achieving either a pumpable or a grindable residue.

While in a plant environment, it might be possible that residue could become wet from rain or snow prior to grinding. A small chunk of heat-treated residue from Run 6430-4P was immersed in distilled water for two days, air dried for one day, and was still brittle and grindable. Thus rain water will not adversely affect residue grindability.

The analysis of another IPA Plant material, shown in Table 8, was very similar to that of first IPA Plant residue (Run 6430-4P in Table I) which was subjected to similar conditions.

These runs fully demonstrate that commercial IPA plant residue has been successfully heat-treated to maintain fluidity, volatilize acetic acid, and decarboxylate High Boilers. The minimum process conditions were a reactor temperature of at least 500° F. and a residence time of about one hour. No external catalysts or other additives, purge gas, or vacuum were required. Residue fluidity was maintained in the absence of the acetic acid melting point depressant because acids were converted to their lower melting anhydride forms at temperatures of at least 500° F. Decarboxylation of acids also aided residue fluidity. At 600° F., 94% of the high molecular weight compounds and 28% of TMLA/HMLA were converted by decarboxylation to low molecular weight acids such as IPA/TA which increased by 36%. The acetic acid normally remaining in the residue was completely recovered. The heat-treated residue appeared to be fluid enough to pump to a holding tank or incinerator at temperatures as low as 500° F. Two viscosity measurements at 500° F. were 270-650 cP which indicated adequate residue fluidity for pumping. The cooled product was very brittle and grindable even when exposed to water. Therefore, it is suitable to pump or grind and air fluidize the heat-treated residue to an incinerator to recover the catalyst metals. Traces of benzene (20–620 ppm) were produced in the condensables as a result of acid decarboxylation. The yield of benzene was always <2 ppm based on the entire residue charged to the reactor. About 75% of the bromine in the residue was vaporized at 600° F. as compared to only about 15% at 500° F. Corrosion problems may be encountered if the residue is heated to the higher temperature at a commercial IPA plant.

TABLE 4

ANALYSIS OF HEAT-TREATED IPA RESIDUE

| Run 6430- | 4J | 4P | 7P | 10P | 18P | 25P | 29P | 36P | 47P |
|---|---|---|---|---|---|---|---|---|---|
| Sample Charge, g. | — | 490 | 509 | 490 | 500 | 500 | 500 | 500 | 500 |
| Heat-up Time (to 500° F.) | — | 270 | 125 | 80 | 60 | 30 | 40 | 40 | 70 |
| Maximum Reactor Temp., °F. | — | 500 | 550 | 600 | 600 | 560 | 550 | 500 | 550 |
| Residence Time at Max. Temp., min. | — | 105 | 55 | 165 | 240 | 60 | 120 | 180 | 310 |
| Condenser Oil Temp., °F. | — | 305 | 310 | 310 | 334 | 220 | 220 | 220 | 220 |
| Products | | | | | | | | | |
| Weight of Recovered Residue, g. | — | 423 | 433 | 342 | 352 | 405 | 431 | 445 | 429 |
| Weight of Condensables, g. | — | 22 | 15 | 28 | 60 | 38 | 47 | 42 | 48 |
| Weight of $CO_2$ (by difference), g. | — | 45 | 61 | 120 | 88 | 57 | 22 | 13 | 23 |
| Condensables | | | | | | | | | |
| Benzoic Acid, wt. % | — | N/A | N/A | N/A | 2.97 | 3.08 | 2.87 | 2.09 | N/A |
| Benzene, ppm | — | 20 | — | — | 620 | — | — | — | — |
| Recovered Residue | | | | | | | | | |
| Co, wt. % | 0.177 | 0.203 | 0.204 | 0.26 | 0.272 | 0.22 | 0.203 | 0.166 | N/A |
| Mn, wt. % | 1.57 | 1.85 | 1.78 | 2.25 | 2.26 | 1.90 | 1.74 | 1.48 | N/A |
| Br, wt. % | 1.92 | 1.89 | 1.52 | 0.65 | 0.76 | 1.84 | 1.81 | 1.65 | N/A |
| Benzoic Acid, wt. % | 10.71 | 6.75 | 8.56 | 2.09 | 2.97 | 5.96 | 10.15 | 10.01 | N/A |
| Phthalic Acid (OA), wt. % | 2.66 | 2.02 | 2.15 | 1.28 | 1.11 | 1.96 | 2.47 | 2.56 | N/A |
| IPA/TA, wt. % | 30.58 | 35.93 | 33.03 | 41.54 | 40.43 | 39.47 | 38.58 | 34.31 | N/A |
| TMLA/HMLA, wt. % | 10.48 | 9.21 | 8.15 | 7.54 | 8.10 | 9.92 | 8.56 | 8.81 | N/A |
| High Molecular Weight Compounds, wt. % | 15.36 | 12.25 | 6.85 | 0.997 | 0.95 | 12.98 | 10.86 | 16.9 | N/A |
| Trace Acetic Acid, wt. % | 3.51 | 0.033 | 0.026 | 0.029 | 0.019 | 0.035 | 0.091 | 0.10 | N/A |
| Viscosity at 500° F., CP | — | — | 650 | — | — | 270 | — | — | — |
| Grinding Rank[1] | (2) | 11 | 4 | 2 | — | 8 | 4 | 14 | — |
| Residue not Accounted for, wt. % | 23.03 | 29.86 | 37.73 | 43.36 | 43.13 | 25.72 | 25.54 | 24.01 | — |

N/A = Not Analyzed
[1]Grinding test described in Experimental Section. Lower numbers denote easier grinding.
(2) Starting material too tacky to grind.

TABLE 5

RETENTION OF BENZOIC ACID IN THE REACTOR

| Run 6430- | 25P | 29P | 36P | 4P | 7P | 10P |
|---|---|---|---|---|---|---|
| Run Type | Cooler Reflux Condenser | | | Low Reactor Temp. Shorter Residence Time | | Highest Reactor Temp. High Temp. Reflux |
| Reactor Max. Temp., °F. | 560 | 550 | 500 | 500 | 550 | 600 |
| Residence Time, min. | 60 | 120 | 180 | 105 | 55 | 165 |
| Condenser Temp., °F. | 220 | 235 | 225 | 305 | 310 | 310 |
| Benzoic Acid in Residue, wt. % | 5.96 | 10.15 | 10.01 | 6.75 | 8.56 | 2.09 |

TABLE 6

REDUCTION OF HIGH MOLECULAR WEIGHT COMPOUNDS IN RESIDUE THROUGH THERMAL DECARBOXYLATION

| Run 6430- | 4J | 4P | 7P | 10P |
|---|---|---|---|---|
| Run Type | Starting Material | More Severe Thermal Conditions | | |
| Reactor Max. Temp., °F. | 0 | 500 | 550 | 600 |
| Residence Time, min. | 0 | 105 | 55 | 165 |
| Loss in Residue, wt. % | 0 | 14 | 15 | 30 |
| Residue Composition, wt. % | | | | |
| TA/IPA | 30.58 | 35.93 | 33.03 | 41.54 |
| HMLA/TMLA | 10.48 | 9.21 | 8.15 | 7.54 |
| High Molecular Weight Compounds | 15.36 | 12.25 | 6.85 | 0.997 |

TABLE 7

COMPARISON OF RESIDUE COMPOSITION BEFORE AND AFTER THERMAL TREATMENT

GMS In Recovered Residue / GMS In Residue Feed

| Run 6430- | 4P | 7P | 10P | 18P | 25P | 29P | 36P |
|---|---|---|---|---|---|---|---|
| Temp., °F./Res. Time, Min. | 500/105 | 550/105 | 600/165 | 600/240 | 560/60 | 550/120 | 500/180 |
| Component | | | | | | | |
| Co | .99 | .98 | 1.025 | 1.082 | 1.007 | .989 | .835 |
| Mn | 1.02 | .96 | 1.001 | 1.013 | .980 | .955 | .839 |
| Br | .85 | .67 | .236 | .279 | .776 | .813 | .765 |
| BA | .544 | .680 | .136 | .195 | .451 | .817 | .832 |
| OA | .656 | .688 | .336 | .294 | .597 | .800 | .857 |
| IPA/TA | 1.014 | .919 | .948 | .931 | 1.045 | 1.088 | .999 |
| TMLA/HMLA | .759 | .753 | .502 | .544 | .767 | .704 | .748 |
| High Molecular Weight Compounds | .689 | .379 | .045 | .044 | .684 | .609 | .979 |
| Acetic Acid | .008 | .006 | .006 | .004 | .008 | .022 | .025 |
| Unacct. for | 1.119 | 1.394 | 1.314 | 1.319 | .905 | .956 | .928 |

TABLE 8

HEAT TREATMENT OF COMMERCIAL IPA PLANT RESIDUE

| Residue Number | WJ-2407; HD-502 | GM80-12; ED-402 |
|---|---|---|
| Run 6430- | 43 | 44 |
| Sample Charge, g. | 500 | 500 |
| Heat-up Time (to 500° F.) | 90 | 55 |
| Maximum Reactor Temp., °F. | 500 | 500 |
| Residence Time at Max. Temp., min. | 130 | 165 |
| Condenser Oil Temp., °F. | 227 | 228 |
| Products | | |
| Weight of Recovered Residue, g. | 173 | 321 |
| Weight of Condensables, g. | 309 | 158 |
| Recovered Residue | | |
| Co, wt. % | N/A | 0.312 |
| Mn, wt. % | N/A | 0.83 |
| Br, wt. % | N/A | 0.61 |
| Benzoic Acid, wt. % | N/A | 6.58 |
| Phthalic Acid (OA), wt. % | N/A | 3.95 |
| IPA/TA, wt. % | N/A | 33.52 |
| TMLA/HMLA, wt. % | N/A | 6.60 |
| High Molecular Weight Compounds, wt. % | N/A | 16.02 |
| Trace Acetic Acid, wt. % | N/A | 0.38 |

We claim:

1. A process for decarboxylation, dehydrating and forming anhydrides from a mixture of water insoluble aldehyde-, carboxy-, methylol-, keto-substituted benzene and toluene moieties derived as oxidation process residues in the oxidation of paraxylene, metaxylene, orthoxylene and pseudocumene to their corresponding di or tricarboxylic acids at elevated temperatures in the presence of manganese, bromine and metal catalyst which process comprises heating such a mixture in the absence of an externally added catalyst at a temperature of about 500° to about 600° F. to produce a fluidizable solid and recovering therefrom entrained hydrocarbon solvent.

2. The process of claim 1 wherein the mixture or water insoluble portion thereof is obtained from the manufacture of isophthalic acid.

3. The process of claim 1 wherein molten residue when cooled to ambient temperature is amenable to grinding to a fluidizable solid.

4. The process of claim 1 wherein the solvent is acetic acid.

5. The process of claim 1 wherein the heating is conducted in the presence of air or oxygen in an inert gas.

6. A continuous process for decarboxylation, dehydrating and forming anhydrides from a mixture of water insoluble aldehyde-, carboxy-, methylol-, keto-substituted benzene and toluene moieties derived as oxidation process residues in the oxidation of paraxylene, metaxylene, orthoxylene and pseudocumene to their corresponding di or tricarboxylic acids at elevated temperatures in the presence of manganese, bromine and metal catalyst which process comprises heating such a mixture in the absence of an externally added catalyst at a temperature of about 500° to 600° F. to produce a fluidizable solid and recovering therefrom entrained hydrocarbon solvent.

7. The process of claim 6 wherein the mixture or water insoluble portion thereof is obtained from the manufacture of isophthalic acid.

8. The process of claim 6 wherein molten residue when cooled to ambient temperature is amenable to grinding to a fluidizable solid.

9. The process of claim 1 or claim 6 wherein the mixture or water insoluble portion thereof is obtained from the manufacture of terephthalic acid.

10. The process of claim 1 or claim 6 wherein the mixture or water insoluble portion thereof is obtained from the manufacture of trimellitic acid.

11. The process of claim 6 wherein the heating is conducted in the presence of air or oxygen in an inert gas.

12. The process of claim 6 wherein the mixture or water insoluble portion thereof is obtained from the manufacture of terephthalic acid.

13. The process of claim 6 wherein the mixture or water insoluble portion thereof is obtained from the manufacture of trimellitic anhydride.

* * * * *